US008664181B2

(12) United States Patent
Kratz et al.

(10) Patent No.: US 8,664,181 B2
(45) Date of Patent: *Mar. 4, 2014

(54) DUAL ACTING PRODRUGS

(75) Inventors: Felix Kratz, Ehrenkirchen (DE); Irmgard Merfort, Freiburg (DE)

(73) Assignee: KTB Tumorforschungsgesellschaft mbH, Freiburg im Breisgau (DE)

( * ) Notice: Subject to any disclaimer, the term of this patent is extended or adjusted under 35 U.S.C. 154(b) by 470 days.

This patent is subject to a terminal disclaimer.

(21) Appl. No.: 12/525,480

(22) PCT Filed: Feb. 15, 2008

(86) PCT No.: PCT/EP2008/001188
§ 371 (c)(1),
(2), (4) Date: Feb. 11, 2010

(87) PCT Pub. No.: WO2006/098789
PCT Pub. Date: Aug. 21, 2008

(65) Prior Publication Data
US 2010/0144647 A1    Jun. 10, 2010

(30) Foreign Application Priority Data
Feb. 16, 2007 (EP) ..................... 07003342

(51) Int. Cl.
| C07K 14/00 | (2006.01) |
| C07K 7/64 | (2006.01) |
| A61K 38/00 | (2006.01) |
| A61K 38/14 | (2006.01) |
| A61K 38/16 | (2006.01) |
| A61K 31/395 | (2006.01) |
| A61K 31/437 | (2006.01) |
| A61K 31/704 | (2006.01) |
| A61K 31/7105 | (2006.01) |
| A61K 49/00 | (2006.01) |

(52) U.S. Cl.
USPC ........... 514/19.2; 514/19.3; 514/50; 530/300; 530/317; 530/322; 530/350

(58) Field of Classification Search
CPC .......... C07K 14/00; C07K 7/64; A61K 38/00; A61K 38/14; A61K 38/16; A61K 31/395; A61K 31/437; A61K 31/704; A61K 31/7105; A61K 47/48338; A61K 47/48407; A61K 49/00
USPC .......... 514/19.2, 19.3, 50; 530/300, 317, 322, 530/350
See application file for complete search history.

(56) References Cited
U.S. PATENT DOCUMENTS
5,595,756 A * 1/1997 Bally et al. .................... 424/450

FOREIGN PATENT DOCUMENTS
| EP | 1 183 050 B1 | 9/2006 |
| EP | 1 704 864 A2 | 9/2006 |
| WO | WO 00/76551 A2 | 12/2000 |
| WO | WO 01/68142 A1 | 9/2001 |
| WO | WO 2006/092229 A1 | 9/2006 |
| WO | WO 2006/092230 A2 | 9/2006 |
| WO | WO 2007/022494 A2 | 2/2007 |
| WO | WO 2008/012086 A2 | 1/2008 |
| WO | WO 2008/098788 A2 | 8/2008 |

OTHER PUBLICATIONS

Definition of derivative from http://cancerweb.ncl.ac.uk/omd/about. html, pp. 1-5. Accessed Jul. 7, 2005.*
Machine translation of WO 01/68142, pp. 1-11. WO 01/68142 published Sep. 20, 2001.*
Sporn MB, Suh N, "Chemoprevention of Cancer," Carcinogenesis, 2000, 21(3); 525-530.*
Auerbach R, Akhtar N, Lewis RL, Shinners BL, "Angiogenesis assays: Problems and pitfalls," Cancer and Metastasis Reviews, 2000, 19: 167-172.*
Gura T, "Systems for Identifying New Drugs Are Often Faulty," Science, 1997, 278(5340): 1041-1042.*
Jain RK, "Barriers to Drug Delivery in Solid Tumors," Scientific American, Jul. 1994, 58-65.*
Neidle, Stephen, ed, Cancer Drug Design and Discover, Elsevier/Academic Press, 2008, pp. 427-431.*
Steinman L, Zamvil SS, "How to successfully apply animal studies in experimental allergic encephalomyelitis to research on multiple sclerosis," Ann. Neurol. 2006, 60: 12-21.*
Sriram S, Steiner I, "Experimental allergic encephalomyelitis: a misleading model of multiple sclerosis," Ann. Neurol. 2005, 58: 939-945.*
Multiple sclerosis from NINDS multiple sclerosis Information page, pp. 1-3. accessed Jul. 23, 2012.*
Andersen, et al., "Radio- and Fluorescence-Labelling of Thapsigargin, A Selective Inhibitor of Microsomal Calcium-ATPase", *J. of Labelled Compounds and Radiopharm.*, vol. XXXI, No. 3, pp. 199-206, (1991).
Bagnato, et al., "Synthesis and Characterization of a Cobalamin-Colchicine Conjugate as a Novel Tumor-Targeted Cytotoxin", *J. Org. Chem.*, vol. 69, pp. 8987-8996, (2004).
Beyer, et al., "Synthese von neuen bifunktionellen Maleinimidverbindungen zur Herstellung von Chemoimmunokonjugaten", *Monatshefte für Chemie*, vol. 128, pp. 91-102, (1997).
Cernuda-Morollón, et al., "15-Deoxy-$\Delta^{12, 14}$-prostaglandin $J_2$ Inhibition of NF-κB-DNA Binding through Covalent Modification of the p50 Subunit", *J. of Biol. Chem.*, vol. 276, No. 38, pp. 35530-35536, (2001).
Dolman, et al. "Stable Golgi-Mitochondria Complexes and Formation of Golgi $Ca^{2+}$ Gradients in Pancreatic Acinar Cells", *J. of Biol. Chem.*, vol. 280, No. 16, pp. 15794-15799, (2005).
Dupuis, et al. "Allergic Contact Dermatitis to α-Methylene-γ-Butyrolactones", *Molecular Immunology*, vol. 17, pp. 1045-1051, (1980).

(Continued)

*Primary Examiner* — Julie Ha
(74) *Attorney, Agent, or Firm* — McDonnell Boehnen Hulbert & Berghoff LLP

(57) ABSTRACT

A prodrug comprising at least two different pharmaceutically and/or diagnostically active compounds independently bound by cleavable linkers and a protein-binding moiety which is capable of binding to carrier a molecule is described.

5 Claims, 5 Drawing Sheets

(56) References Cited

OTHER PUBLICATIONS

Ehlhardt, et al., "Liquid Chromatography/Nuclear Magnetic Resonance Spectroscopy and Liquid Chromatography Mass Spectrometry Identification of Novel Metabolites of the Multidrug Resistance Modulator LY335979 in Rat Bile and Human Liver Microsomal Incubations", *Drug Metabolism and Disposition,* vol. 26, No. 1, pp. 42-51, (1997).

Gabriel-Robez, et al., "Allergic Contact Dermatitis to Methylenelactones Use of Lymphocyte Transformation Test", *Arch. Dermatol. Res.,* vol. 272, pp. 73-78, (1982).

De Groot, et al., "Design, Synthesis, and Biological Evaluation of a Dual Tumor-specific Motive Containing Integrin-targeted Plasmin-cleavable Doxorubicin Prodrug", *Mol. Can. Ther.,* vol. 1, pp. 901-911, (2002).

Hua, et al., "Synthesis and Interaction of Fluorescent Thapsigargin Derivatives with the Sarcoplasmic Reticulum ATPase Membrane-Bound Region", *Biochemistry,* vol. 34, No. 15, pp. 5137-5142, (1995).

Kratz, et al., "Development of Albumin-binding Doxorubicin Prodrugs that are Cleaved by Prostate-specific Antigen", *Arch. Pharm. Chem. Life Sci.,* vol. 338, pp. 462-472, (2005).

Kratz, et al., "Preparation, Characterization and in Vitro Efficacy of Albumin Conjugates of Doxorubicin", *Biol. Pharm. Bull.,* vol. 21, No. 1, pp. 56-61, (1998).

Krüger, et al., "Synthesis and Stability of Four Maleimide Derivatives of the Anticancer Drug Doxorubicin for the Preparation of Chemoimmunoconjugates", *Chem. Pharm. Bull.,* vol. 45, No. 2, pp. 399-401, (1997).

Marastoni, et al., "P3 and P4 position analysis of vinyl ester pseudopeptide proteasome inhibitors", *Bioorg. & Med. Chem. Letters,* vol. 16, pp. 3125-31300, (2006).

Marastoni, et al., "Synthesis and biological evaluation of new vinyl ester pseudotripeptide proteasome inhibitors", *Eur. J. Med. Chem.,* vol. 41, pp. 978-984 (2006).

Molema, et al. "Targeting of drugs to various blood cell types using (neo-)glycoproteins, antibodies and other protein carriers", *Advanced Drug Delivery Reviews,* vol. 14, pp. 25-50, (1994).

Pérez-Sala, et al., "Contribution of Covalent Protein Modification to the Antiinflammatory Effects of Cyclopentenone Prostaglandins", *Ann. N.Y. Acad. Sci.,* vol. 973, pp. 533-536, (2002).

Reddy, et al., "Folate receptor targeted anti-tumor activity of EC-0225, a folate-targeted dual drug conjugate", *Proc. Of the Amer. Assoc. for Can. Res. Ann. Meeting,* vol. 47, p. 135, (2006) (Abstract).

Teodori, et al., "Synthesis and Binding Properties of Photoactivable Biotin-Conjugated Verapamil Derivatives for the Study of P-170 Glycoprotein", *Bioorg. & Med. Chem.,* vol. 7, pp. 1873-1880, (1999).

Thaden, et al., "Photoaffinity Behavior of a Conjugate of Oligonucleoside Methylphosphonate, Phodamine, and Psoralen in the Presence of Complementary Oligonucloetides", *Bioconjugate Chem.,* vol. 4, pp. 386-394, (1993).

Vlashi, et al., "Folate Targeted Chemotherapeutics and Their Size-Dependent Penetration into Solid Tumor Mass.", *Abstracts of Papers of Amer. Chem. Soc.,* vol. 229, No. 2, p. U197, (2005) (Abstract No. 492).

Wan, et al., "Novel multi-component nanopharmaceuticals derived from poly(ethylene) glycol, retro-inverso-Tat nonapeptide and saquinavir demonstrate combined anti-HIV effects", *AIDS Research and Therapy,* vol. 3, No. 12, pp. 1-15, (2006).

Willner, et al., "(6-Maleimidocaproyl)hydrazone of Doxorubicin—A New Derivative for the Preparation of Immunoconjugates of Doxorubicin", *Bioconjugate Chem.,* vol. 4, pp. 521-527, (1993).

Yang, et al., "Evaluation of disulfide reduction during receptor-mediated endocytosis by using FRET imaging", *PNAS,* vol. 103, No. 37, pp. 13872-13877, (2006).

Yang, et al., "Folate-functionalized polymeric micelles for tumor targeted delivery of a potent multidrug-resistance modulator FG020326", *J. of Biomed. Mater. Res. Part A,* vol. 86, No. 1, pp. 48-60, (2007).

* cited by examiner

DUAL ACTING PRODRUGS

The present invention relates to a prodrug which comprises at least two different pharmaceutically and/or diagnostically active compounds independently bound by cleavable linkers and a protein-binding moiety which is capable of binding to carrier a molecule.

Most of the drugs used at present are compounds having low molecular weights and exhibit, when systemically administered to a patient, a high plasma clearance or total body clearance. Furthermore, said low molecular weight compounds show a high tendency to penetrate body tissues by diffusion, resulting in a uniform bio-distribution. These are the two main reasons why only small quantities of the drug reach the site of action and, due to distribution over healthy tissues of the body, said drugs give rise to problematic side-effects. These disadvantages are of particular concern for those drugs having a high cytotoxic potential, such as cytotoxic agents, immunosuppressive agents or virostatic agents.

Several strategies have been pursued for improving the selectivity of low molecular weight drugs and thus to increase the concentration of the active agent in the desired tissue, while the concentration of the same is decreased in healthy tissues in order to reduce side-effects.

Carriers, such as for example albumin, or its drug conjugates exhibit a markedly long half-life in the systemic circulation of up to 19 days (cf. Peters, T. J., "Serum Albumin", *Adv. Protein. Chem.*, 1985, 37, 161-245). Because of an elevated permeability of vessel walls of the e.g. malignant, infected or inflamed tissue for macromolecules, the carrier, such as for example serum albumin, passes preferentially into the target tissue (cf. Maeda, H., Mastumura, Y., *Crit. Rev. Ther. Drug Carrier Sys.*, 1989, 6, 193-210). In this context, prodrugs have been presented which bind in situ to e.g. human serum albumin and show improved properties in contrast to the drug alone (cf. DE 103 10 082 A1 and DE 10 2005 009 084 A1).

In addition, antibodies, peptides or synthetic polymers have been investigated as drug carriers for the development of prodrugs (Kratz et al., (2001): Anticancer drug conjugates with macromolecular carriers, in Polymeric Biomaterials, second edition, ed. S. Dumitriu, Marcel Dekker, New York, Chapter 32, 851-894; R. Duncan, *Nat. Rev. Drug Discovery* 2003, 347-360).

However, although such prodrugs have been shown to allow a more specific delivering of the active agent to the target tissue in most cases, a variety of biochemical mechanisms is known which lead to a decreased efficacy of the respective drug.

For example, intrinsic or acquired multidrug resistance (MDR) is a major problem in the treatment of many cancers. A number of biochemical mechanisms have been described that are responsible for the multidrug resistance phenotype that include changes in the cellular target of the respective drug, alterations in enzymatic activation, detoxification mechanisms or cell cycle checkpoints, defective apoptotic pathways or insensitivity to apoptosis, membrane changes as well as elimination of the drug from the tumor cell through the action of drug efflux pumps. Many studies have evaluated the cellular resistance mechanisms, e.g. in breast cancer, that are mediated by the cell-membrane efflux pumps P-Glycoprotein, Multiple Resistance Protein (MRP) and Breast Cancer Resistance Protein (BCRP) which belong to the ATP-binding cassette (ABC) transporter family (Ling et al., Cancer Chemother. Pharmacol., 1997, 40: 3-8; Borst et al., Biochim. Biophys. Acta, 1999, 1461:347-357; Thomas and Coley, Cancer Control, 2003, 10:159-165, Wang, J. Clin. Pharm. Ther., 2003, 28:203-228; Leonessa and Clark, Endocrine-Related Cancer, 2003, 10(1):43-73).

Another example relates to the transcription factor NF-κB which plays a key role in the development and progression of tumors, since it controls several signalling pathways in apoptotic, cell cycle and cell migration processes. The overexpression of NF-κB which is triggered inherently or in the presence of cytostatic agents prevents apoptosis in tumor cells and is thus responsible for the development of chemoresistance.

Therefore, a need exists for improved drugs which enable the treatment and/or diagnosis of a disease in a patient, and which avoid or at least reduce the above-described disadvantages.

In view of the above, the technical problem underlying the present invention is to provide novel prodrugs which should act by a dual acting principle through additive or synergistic effects, e.g. by modulating cellular functions or chemosensitizing, thus improving the effect of the respective drugs.

According to the present invention, the above problem is solved by providing a dual acting prodrug comprising
(i) at least a first pharmaceutically and/or diagnostically active compound,
(ii) at least a second pharmaceutically and/or diagnostically active compound,
(iii) two or more cleavable linkers, and
(iv) a protein-binding moiety,
wherein the first and the second pharmaceutically and/or diagnostically active compounds are each bound to a cleavable linker, and
wherein the first and the second pharmaceutically and/or diagnostically active compounds are different from each other.

According to the present invention, there is no specific restriction as to how the components, i.e. the pharmaceutically and/or diagnostically active compounds, the cleavable linkers and the protein-binding moiety, of the above-defined prodrug are connected to each other, as long as each of the pharmaceutically and/or diagnostically active compound is bound to a cleavable linker and the biological function of the protein-binding moiety and the pharmaceutically and/or diagnostically active agents are not negatively affected by the structure set up. The molecular structure of the prodrug of the present invention may for example have a linear form or a branched form or is present in a circular form.

According to the present invention, there is no specific restriction concerning the structural setup of the prodrug of the present invention; i.e. the way the constituents as outlined under above items (i) to (iv) of the above-defined prodrug are chemically bonded together. In particular, the prodrug according to the present invention may contain one or more spacers in any position between the constituents of the above-defined prodrug, i.e. the protein-binding moiety may for example be bound to the rest of the prodrug through a spacer or, as another example, the first pharmaceutically and/or diagnostically active compound may be bound to the at least one cleavable linker through a spacer. Furthermore, the function of e.g. the cleavable linker may be incorporated in such a spacer, i.e. a spacer may be used between the pharmaceutical and/or diagnostically active compound which can also serve as the cleavable linker. It is also possible to bind the pharmaceutically and/or diagnostically active compound, the cleavable linker, and/or the protein-binding moiety to a central group, which may be linear or branched, such as a peptide, a sugar, a heterocyclic group, or any inorganic or organic compound suitable to bind one or more of the constituents of the prodrug.

The term "prodrug" as used herein means any form of a drug which is administered to an organism, such as a human, in an inactive or less active form and is converted, e.g. by metabolization, into the active form. Said conversion of the prodrug into the active form is not specifically restricted and includes any chemical and/or physical alteration of the prodrug which occurs after administration, such as for example release of an active part of the prodrug at the site of action.

The expression "pharmaceutically active compound" means any compound which brings about a pharmacological effect either by itself or after its conversion in the organism in question, and thus also includes the derivatives from these conversions. The pharmacological effect of the pharmaceutically active compound according of the present invention can be a single effect only, e.g. a cytostatic effect, or a broad pharmacological spectrum of action, such as an immunosuppressive and antiphlogistic effect at the same time.

The expression "diagnostically active compound" used herein is not specifically restricted and includes any compound which can be detected and preferably quantified, in an organism or parts thereof, such as for example cells and/or fluids, such as for example the serum, through suitable chemical and/or physical measurement methods.

The expression "cleavable linker" means any linker which can be cleaved physically or chemically. Examples for physical cleavage may be cleavage by light, radioactive emission or heat, while examples for chemical cleavage include cleavage by redox-reactions, hydrolysis, pH-dependent cleavage or cleavage by enzymes.

According to a preferred embodiment of the present invention, the cleavable linker comprises one or more hydrolytically cleavable bonds, the hydrolysis of which releases the pharmaceutically and/or diagnostically active compounds. Examples for hydrolytically cleavable bonds are ester bonds or metal-complex bonds, such as are present in platinum-dicarboxylate complexes, where a diaminediaquoplatinum (II) complex is liberated.

In another preferred embodiment of the present invention, the cleavable linker may be cleavable by an enzyme. For example, the cleavable linker of the present invention may contain at least one peptide bond which preferably lies within a cleavable peptide sequence of a protease. A peptide bond can therefore be implemented by the insertion of a respective peptide sequence into the cleavable linker. Suitable enzymes are, for example, proteases and peptidases, e,g. matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. Preferred examples of proteases according to the present invention are in particular MMP-2, MMP-3 and MMP-9, cathepsin B, H, L and D, plasmin, urokinase, and prostate-specific antigen (PSA). Preferred peptide sequences that are incorporated in the prodrug are: Arg, Arg-Arg, Phe-Arg, Phe-Cit, Ile-Pro Lys, Lys-Lys, Arg-Lys, Ala-Leu-Ala-Leu [SEQ ID NO:1], Phe-Lys, Phe-Lys-Ala, Val-Cit, Val-Arg, Ala-Phe-Lys, D-Ala-Phe-Lys, Met, Met-Met, Phe-Met, Tyr-Met, Ala-Met, Ala-Phe-Met, Phe-Ala-Met, Ala-Tyr-Met, Phe-Tyr-Met, Ser-Ser-Tyr-Tyr-Ser-Arg [SEQ ID NO:2], Phe-Pro-Lys-Phe-Phe-Ser-Arg-Gln [SEQ ID NO:3], Lys-Pro-Ile-Glu-Phe-Nph-Arg-Leu [SEQ ID NO:4], Gly-Pro-Leu-Gly-Ile-Ala-Gly-Gln [SEQ ID NO:5], Gly-Pro-Leu-Gly-Ile-Ala-Gly-Gln [SEQ ID NO:6], and Gly-Phe-Leu-Gly [SEQ ID NO:7]. In addition, the enzymatically cleavable linker may contain a self-immolative linker such as a self-immolative p-aminobenzyloxycarbonyl (PABC) linker or a N-methyl- or symmetric N,N-dimethylethylene linker.

In another embodiment of the present invention, the cleavable linker according to the present invention preferably contains at least one acid-labile bond. Examples of acid-labile bonds are ester, acetal, ketal, imine, hydrazone, carboxylhydrazone and sulfonylhydrazone bonds and bonds containing a trityl group.

According to the present invention, in case the pharmaceutically and/or diagnostically active compound is a diagnostically active agent which does not need to be cleaved, the cleavable linker may be chosen to comprise only such bonds which are difficult to cleave under physiological conditions such as an amide bond, carbon-carbon bonds or bonds between carbon and a heretoratom, wherein the heteroatom may be selected from O, N, S or P.

The term "protein-binding moiety" used herein is not specifically restricted and means any functional group which is capable of binding to an amino, a hydroxy or thiol group of a compound which may be of endogenous or exogenous origin. Preferred examples of a protein-binding moiety according to the present invention are a maleinimide group, a halogenacetamide group, a halogenacetate group, a pyridylthio group, a vinylcarbonyl group, an aziridin group, a disulfide group, a substituted or unsubstituted acetylene group, a hydroxysuccinimide ester group. The protein-binding group also includes functional groups, such as —COOH or $SO_3H$, that can be activated by standard coupling agents, e.g. dicyclocarbodiimides, acid chlorides, or peptide coupling reagents (e.g., BOP, HATU, PyBOP).

One or several prodrugs can be bound to any suitable carrier such as peptides, sugars, serum proteins, antibodies or antibody fragments, growth factors, polysaccharides, or synthetic polymers. The carrier in general contains suitable functional groups such as hydroxy, amino or thiol groups to bind the protein-binding prodrug. If necessary, these can be introduced in the carrier molecule by chemical modification through techniques known to those skilled in the art (Kratz et al., (2001): Anticancer drug conjugates with macromolecular carriers, in Polymeric Biomaterials, second edition, ed. S. Dumitriu, Marcel Dekker, New York, Chapter 32, 851-894).

In a preferred embodiment, the protein-binding moiety of the prodrug according to the present invention allows said prodrug to bind in situ after administration by e.g. injection, to components of body fluids and/or tissue components, preferably to serum proteins and more preferably to serum albumin, particularly to cysteine-34 of serum albumin and are then present as macromolecular prodrugs which carry the pharmaceutically and/or diagnostically active compounds to the target site.

In a further preferred embodiment, the protein-binding moiety of the above-defined prodrug binds in situ to cysteine-34 of albumin.

According to the present invention, the term "in situ" includes the binding of the prodrug according to the present invention to an endogenous biomolecule, such as a serum protein, particularly serum albumin, inside the organism to which the prodrug has been administered.

According to one embodiment of the present invention, in the prodrug as defined above the first and second pharmaceutically and/or diagnostically active compounds are independently selected from the group consisting of a cytostatic agent, a cytokine, an immunosuppressant, an antirheumatic, an antiphlogistic, an antibiotic, an analgesic, a virostatic, or an antimycotic agent, a transcription factor inhibitor, a cell cycle modulator, a MDR modulator, a proteasome or protease inhibitor, an apoptosis modulator, an enzyme inhibitor, an angiogenesis inhibitor, a hormone or hormone derivative, a radioactive substance, a light emitting substance, or a light absorbing substance.

Especially suitable cytostatic agents according to the present invention are the N-nitrosoureas such as nimustine, the anthracyclines doxorubicin, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites, for example purine antagonists or pyrimidin antagonists, such as 5-fluorouracil, 2'-deoxy-5-fluorouridine, cytarabine, cladribine, fludarabine, pentostatine, gemcitabine and thioguanine, and any derivatives thereof; folic acid antagonists such as methotrexate, or raltitrexed, pemetrexed or plevitrexed, the taxanes paclitaxel and docetaxel, and any derivatives thereof; the camptothecins topotecan, irinotecan, 9-aminocamptothecin and camptothecin, and any derivatives thereof; the Vinca alkaloids vinblastine, vincristine, vindesine and vinorelbine, and any derivatives thereof; calicheamicins; maytansinoids; auristatins, epothilones, bleomycin, dactinomycin, plicamycin, mitomycin C and cis-configured platinum(II) complexes.

Especially suitable cytokines according to the present invention are, for example, interleukin 2, interferon α-2a, interferon α-2b, interferon β-1a, interferon β-1b, interferon γ-1b, tumor necrosis factor, and any derivatives thereof.

Especially suitable immunosuppressants according to the present invention are, for example, cyclosporin A, tacrolimus, sirolimus, everolimus, mycophenolatmofetil, and any derivatives thereof.

Especially suitable antirheumatics according to the present invention are, for example, methotrexate, leflunomid, sulfasalazine, chloroquine, and any derivatives thereof.

Especially suitable antiphlogistics and/or analgesics according to the present invention are, for example, salicylic acid derivatives such as for example acetylsalicylic acid, and any derivatives thereof; drug derivatives having an acetic or propionic acid group such as diclofenac or, respectively, naproxen, and aminophenol derivatives such as for example paracetamol.

Especially preferred antibiotics according to the present invention are, for example, sulfanilamide, sulfacarbamide and sulfamethoxydiazine, and any derivatives thereof; penicillins, for example 6-aminopenicillanic acid, penicillin G as well as penicillin V, and any derivatives thereof; isoxazolyl-penicillins such as oxacillin, cloxacillin and clucloxacillin, and any derivatives thereof; α-substituted benzylpenicillins such as ampicillin, carbenicillin, pivampicillin, amoxicillin, and any derivatives thereof; acylaminopenicillins, for example mezlocillin, azlocillin, piperacillin, apalcillin, and any derivatives thereof; amidinopenicillins, for example mecillinam; atypical β-lactams such as imipenam and aztreonam; cephalosporins, for example cephalexin, cefradin, cefaclor, cefadroxil, cefixime, cefpodoxime, cefazolin, cefazedone, cefuroxime, cefamandole, cefotiam, cefoxitin, cefotetan, cefmetazole, latamoxef, cefotaxmine, ceftriaxone, ceftizoxime, cefmonoxime, ceftazidime, cefsulodin and cefoperazone, and any derivatives thereof; tetracyclines such as tetracycline, chlorotetracycline, oxytetracycline, demeclocycline, rolitetracycline, doxycycline, minocycline, and any derivatives thereof; chloramphenicols such as chloramphenicol and thiamphenicol, and any derivatives thereof; gyrase inhibitors, for example nalidixic acid, pipemidic acid, norfloxacin, ofloxacin, ciprofloxacin and enoxacin, and any derivatives thereof; and antituberculotics such as isoniazid, and any derivatives thereof.

Especially preferred virostatics according to the present invention are, for example nucleoside analogs such as acyclovir, ganciclovir, idoxuridine, ribavirin, vidaribine, zidovudine, didanosine, and 2',3'-dideoxycytidine (ddC), and any derivatives thereof, as well as amantadine.

Especially suitable antimycotic agents according to the present invention are, for example, amphotericin B, and any derivatives thereof.

Especially preferred MDR modulators according to the present invention are verapamil, dihydropyridins, cyclosporin A and D, tacrolismus, rapamyin, digoxin, digitoxin, quinidin, lovastatin, atorvastin, analogues of reserpine, trifluoroperazine, pervilleines A-F, valspodar, dexverapamil, biricodar, bepridil, erythromycin, levofloxacin, losartan, morphin, rifampin, phenytoin, colchicin, rhodamin 123, amprenavir, indinavir, nelfinavir, saqunavir, ritonavir XR9576, LY335979, OC144093, R101933, GF120918, ONT-093, MS-209, S-9788, reversin 205 and 121, or any related derivative.

Especially preferred transcription factor inhibitors according to the present invention are, for example compounds that inhibit activation of NF-κB such as alpha-lipoic acid, alpha-tocopherol, anetholdithiolthione (ADT), butylated hydroxyanisole (BHA), cepharanthine, caffeic acid phenethyl ester (3,4-dihydroxycinnamic acid, CAPE), catechol derivatives, diethyldithiocarbamate (DDC), diferoxamine, dihydrolipoic acid, disulfram, dimethyldithiocarbamates (DMDTC), curcumin (diferuloylmethane), EPC-K1 (phosphodiester compound of vitamin E and vitamin C), epigallocatechin-3-gallate (EGCG; green tea polyphenols), ethylene glycol tetraacetic acid (EGTA), glutathione, L-cysteine, lacidipine, melatonin, N-acetyl-L-cysteine (NAC), nordihydroguaiaritic acid (NDGA), phenanthrolines, pyrrolinedithiocarbamate (PDTC), quercetin, tepoxaline (5-(4-chlorophenyl)-N-hydroxy-(4-methoxyphenyl)-N-methyl-1H-pyrazole-3-propan-amide), vitamin C, vitamin E derivatives, alpha-torphryl succinate, alpha-torphryl acetate, PMC (2,2,5,7,8-pentamethyl-6-hydroxychromane), benzyisocyanate, resveratol, genistein, lupeol, lycopene, panepoxydone, epoxyquinomicin C, dehydroxymethylepoxyquinomicin (DHMEQ), cycloepoxydon, gliotoxin, as well as I-κB-alpha phosphorylation and/or degradation inhibitors such as PS-1, 145, aspirin, salicylic acid, BAY-11-7082 (E3[(4-methylphenyl)-sulfonyl]-2-propenenitrile), BAY-11-7085 (E3[(4-t-butylphenyl)-sulfonyl]-2-propenenitrile), cycloepoxydon; 1-hydroxy-2-hydroxymethyl-3-pent-1-enylbenzene, ibuprofen, prostaglandin A1, sanguinarine (pseudochelerythrine, 13-methyl-[1,3]-benzodioxolo-[5,6-c]-1,3-dioxolo-4,5 phenanthridinium), sulfasalazine, sulindac, capsaicin (8-methyl-N-vanillyl-6-nonenamide), emodin (3-methyl-1,6,8-trihydroxyanthraquinone), erbstatin (tyrosine kinase inhibitor), estrogen (E2), gliotoxin, genistein, resiniferatoxin, and miscellaneous inhibitors of NF-κB such as beta-amyloid protein, glucocorticoids (dexamethasone, prednisone, methylprednisolone), leptomycin B (LMB), o,o'-bismyristoyl thiamine disulfide (BMT), ADP ribosylation inhibitors e.g., nicotinamide, 3-aminobenzamide, bi-, tri, or tetracyclic lactames, 1,8-naphtalimide derivatives, phenanthridin-6-ones, 3,4-dihydro-5-methyl-isoquinolin-1(2H)-one, benzoxazole-4-carboxamide, 1,6-naphthyridine-5(6H)-ones, quinazolin[3,4-d]pyrimidin-4(3H)-ones, 1,5-dihydroxyisoquinoline, 2-methyl-quinazolin-4[3H]-ones, 1,11b-dihydro-[2H]benzopyrano [4,3,2-de]isoquinolin-3-one, atrial natriuretic peptide (ANP), atrovastatin (HMG-CoA reductase inhibitor), calcitriol (1a,25-dihydroxyvitamine D3), E3330 (quinone derivative), herbimycin A, hypericin, hydroquinone (HQ), KT-90 (morphine synthetic derivatives), mevinolin, 5'-methylthioadenosine (MTA), pentoxifylline (1-(5'-oxohexyl) 3,7-dimethylxanthine, PTX), phenyl-N-tert-butylnitrone (PBN), pituitary adenylate cyclase-activating polypeptide (PACAP), quinadril (ACE inhibitor), ribavirin, secretory leukocyte protease inhibitor (SLPI), serotonin derivative (N-(p-coumaroyl) serotonin,), silymarin, vasoactive intestinal peptide (VIP), D609 (phosphatidylcholine-phospholipase C inhibitor), RO31-8220 (PKC inhibitor), SB203580 (p38 MAPK inhibitor), triptolide (PG490, extract of Chinese herb), LY294,002, mesalamine, wortmannin (fungal metabolite), or CHS 828 (N-(6-(p-chlorophenoxy)-hexyl)-N'-cyano-N"-4-pyridylguanidine), sesquiterpene lactones such as parthenoilde, helenalin, miller-9E-enolid and budlein A.

Especially preferred proteasome and protease inhibitors according to the present invention are, for example peptide aldehydes: ALLnL (N-acetyl-leucinyl-leucinyl-norleucynal, MG101), LLM (N-acetyl-leucinyl-leucinyll-methional), Z-LLnV (carbobenzoxyl-leucinyl-leucinyl-norvalinal, MG115), Z-LLL (carbobenzoxyl-leucinyl-leucinyl-leucynal, MG132), Z-LLL-B(OH)$_2$ (MG-262), boronic acid derivatives, e.g. PS-273, PS-293, PS-296, PS-303, PS-305, PS-313, PS-321, PS-325, PS-334, PS-341, PS-364, PS-352, PS-383, lactacystine, beta-lactone, boronic acid peptide, ubiquitin ligase inhibitors deoxyspergualin, APNE (N-acetyl-DL-phenylalanine-beta-naphthylester), BTEE (N-benzoyl L-tyrosine-ethylester), DCIC (3,4-dichloroisocoumarin), DFP (diisopropyl-uorophosphate), TPCK (N-alpha-tosyl-L-phenylalanine chloromethyl ketone), TLCK (N-alpha-tosyl-L-lysine chloromethyl ketone), FK506 (Tacrolimus), Cyclosporin A.

Especially preferred apoptosis modulators according to the present invention are, for example farnesyl transferase inhibitors, e.g. R115777, SCH66336, BMS214662, Imatinib, 17-AAG, EGFR inhibitors, e.g., ZD1839, MEK inhibitors, e.g., PD 032590, RAF inhibitors e.g., BAY43-9006, erlotinib, PKC inhibitors, e.g. UCN-01, PKC-412, Bryostatin, ISIS-3521, LY333531, safingol, CGP-41251 (midostaurin), HDAC inhibitors, e.g., suberoyl-3-aminopyridineamide hydroxamic acid, lonidamine, apoptin, survivin, rapamycin, CCI-779, RAD001 (everolimus), PXD101, tyrosine kinase inhibitors, e.g. Iressa, OSI-774, STI-571, inhibitors of enzymes in the mitogen-activated protein kinase pathway e.g., PD-098059, U-0126.

Especially preferred cell cycle modulators according to the present invention are, for example flavopiridol, bryostain-1, roscovitine, BMS-387032, perifosine, or lovastatin.

Especially preferred enzyme inhibitors according to the present invention are, for example inhibitors of gamma-glutamyl cystine synthetase e.g., buthione, sulfoxime.

Especially preferred angiogenesis inhibitors according to the present invention are, for example thalidomide, endostatin, celecoxib, ABT-510, combrestatin A4, dalteparin, dimethylxanthenone acetic acid, lenalidomide, LY317615 (enzastaurin), PPI-2458, ADH-1 (exherin), AG-013736, AMG-706, AZD2171, Bay 43-9006 (sorafenib), BMS-582664, CHIR-265, GW786034 (pazopanib), PI-88, PTK787/ZK 222584 (vatalanib), RAD001 (everolimus), SU11248 (sunitinib), suramin, XL184, ZD6474, ATN-161, or EMD 121974 (cilenigtide).

Especially preferred hormones or hormone derivatives according to the present invention are, for example aminogluthemid, buserilin, cyproteronacetate, droloxifen, ethinylestradiol, flutamid, formesta, fosfestrol, gestonoroncaproate, goserilin, leuprolein, lynestrenol, medrogeston, medroxyprogesteronacetate, megestrolactetate, octreotid, tamoxifen, toremifin, triptorelin, anastrazole, exemestane, or letrozone.

For preparing the protein-binding prodrugs of the present invention the first and second pharmaceutically and/or diagnostically active compounds are bound to a bifunctional protein-binding linker through an acid-sensitive and/or hydrolytically and/or enzymatically cleavable bond. This derivatisation is carried out with a suitable functional group of the first and second pharmaceutically and/or diagnostically active compound which is a HO—, NH$_2$—, HOOC—, HO$_3$S—, or carbonyl group. If the first and second pharmaceutically and/or diagnostically active compound does not contain a suitable functional group, then this is introduced through chemical modification; i.e. the above-mentioned first and second pharmaceutically and/or diagnostically active compounds additionally include all derivatives that possess a HO—, NH$_2$—, HOOC—, HO$_3$S—, and/or carbonyl group.

In the prodrugs of the present invention the two or more cleavable linkers of the above-defined prodrug can independently be cleaved hydrolytically and/or enzymatically and/or pH-dependently. According to the present invention, each of the cleavable linkers in the above-defined prodrug may be the same or different. The cleavable linker of the first and of the second pharmaceutically and/or diagnostically active compound may for example both be acid-sensitive or enzymatically cleavable, or according to a further example, the cleavable linker of the first pharmaceutically and/or diagnostically active compound my be an acid-labile linker, while the cleavable linker of the second pharmaceutically and/or diagnostically active compound may be a linker cleavable by an enzyme.

In a preferred embodiment of the present invention, the first pharmaceutically and/or diagnostically active compound of the prodrug as defined above is a cytostatic agent selected from the group consisting of N-nitrosoureas such as nimustine, the anthracyclines doxorubicin, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites, for example purine antagonists or pyrimidin antagonists, such as 5-fluorouracil, 2'-deoxy-5-fluorouridine, cytarabine, cladribine, fludarabine, pentostatine, gemcitabine and thioguanine, and any derivatives thereof; folic acid antagonists such as methotrexate, raltitrexed, pemetrexed or plevitrexed, the taxanes paclitaxel and docetaxel, and any derivatives thereof; the camptothecins topotecan, irinotecan, 9-aminocamptothecin and camptothecin, and any derivatives thereof; the Vinca alkaloids vinblastine, vincristine, vindesine and vinorelbine, and any derivatives thereof, calicheamicins and any derivatives thereof, maytansinoids and any derivatives thereof, auristatins and any derivatives thereof, epothilones and any derivatives thereof, bleomycin, dactinomycin, plicamycin, mitomycin C and cis-configured platinum(II) complexes.

According to another embodiment of the present invention, the second pharmaceutically and/or diagnostically active compound of the prodrug as defined above is a cytostatic agent selected from the group consisting of N-nitrosoureas such as nimustine, the anthracyclines doxorubicin, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites, for example purine antagonists or pyrimidin antagonists, such as 5-fluorouracil, 2'-deoxy-5-fluorouridine, cytarabine, cladribine, fludarabine, pentostatine, gemcitabine and thioguanine, and any derivatives thereof; folic acid antagonists such as methotrexate, raltitrexed, pemetrexed and plevitrexed, the taxanes paclitaxel and docetaxel, and any derivatives thereof; the camptothecins topotecan, irinotecan, 9-aminocamptothecin and camptothecin, and any derivatives thereof; the Vinca alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof, bleomycin, dactinomycin, plicamycin, mitomycin C and cis-configured platinum(II) complexes.

The combination of cytostatic agents is not restricted in any way. Preferred combinations are those that include cytostatic agents that exhibit different modes of action or act synergistically, such as doxorubicin and paclitaxel.

According to another embodiment of the present invention, the second pharmaceutically and/or diagnostically active compound of the above-defined prodrug is a multidrug resistance (MDR) modulator selected from a first generation MDR modulator, a second generation MDR modulator, or a third generation MDR modulator.

According to a specific embodiment of prodrug as defined above, the multidrug resistance (MDR) modulator of the first generation is selected from the group consisting of verapamil, dihydropyridins, cyclosporin A and D, tacrolismus, rapamyin, digoxin, digitoxin, quinidin, or any derivative thereof.

According to another specific embodiment of present invention the multidrug resistance (MDR) modulator of the second generation usable in the prodrug as defined above is selected from the group consisting of lovastatin, atorvastin, analogues of reserpine, trifluoroperazine, pervilleines A-F, valspodar, dexverapamil, biricodar, bepridil, erythromycin, levofloxacin, losartan, morphin, rifampin, phenytoin, colchicin, rhodamin 123, amprenavir, indinavir, nelfinavir, saqunavir, ritonavir, or any derivative thereof.

In another specific embodiment, the multidrug resistance (MDR) modulator usable in the above-defined prodrug of the third generation is selected from the group consisting of XR9576, LY335979, OC-144-093, R101933, GF120918, ONT-093, MS-209, S-9788, reversin 205 and 121, or any related derivative.

In another preferred embodiment of the present invention, the second pharmaceutically and/or diagnostically active compound of the prodrug as defined above is a transcription factor inhibitor modulating NF-κB, comprising compounds capable of inhibiting activation of NF-κB, I-κB-alpha phosphorylation and/or degradation inhibitors, miscellaneous inhibitors of NF-κB as well as proteasome inhibitors.

In another preferred embodiment of the present invention, the second pharmaceutically and/or diagnostically active compound of the prodrug as defined above is a transcription factor inhibitor selected from the group consisting of sesquiterpene lactones.

In a specific embodiment of the above-defined prodrug according to the present invention, the protein-binding moiety is selected from the group consisting of a maleinimide group, a halogenacetamide group, a halogenacetate group, a pyrildylthio group, a vinylcarbonyl group, an aziridin group, a disulfide group, an substituted or unsubstituted acetylene group, or an N-hydroxysuccininide ester group.

According to another embodiment of the present invention, at least one of the first or second pharmaceutically and/or diagnostically active compounds of the prodrug as defined above contains one or more radionuclides, one or more positron emitters, one or more NMR contrast agents, one or more fluorescent compound(s), or one or more near-infrared contrast agents.

According to one specific embodiment, the prodrug as defined above comprises
(i) a cytostatic agent as the first pharmaceutically and/or diagnostically active compound,
(ii) a MDR modulator as the second pharmaceutically and/or diagnostically active compound,
(iii) at least two cleavable linkers, and
(iv) a protein-binding moiety,
wherein the cytostatic and the MDR modulator are each bound to a cleavable linker.

In a specific example of the prodrug as defined above, the cytostatic is doxorubicin, paclitaxel or a camptothecin derivative, the MDR modulator is a p-glycoprotein modulator and the protein-binding moiety is a maleimide derivative.

According to a preferred embodiment of the prodrug as defined above, the cytostatic is camptothecin or a derivative thereof, the MDR modulator is OC144093 and the protein-binding moiety is a maleimide derivative.

According to another specific embodiment of the present invention, the above-defined prodrug comprises
(i) a cytostatic as the first pharmaceutically and/or diagnostically active compound,
(ii) a transcription factor inhibitor as the second pharmaceutically and/or diagnostically active compound,
(iii) at least two cleavable linkers, and
(iv) a protein-binding moiety,
wherein the cytostatic and the transcription factor inhibitor are each bound to a cleavable linker.

In one specific embodiment of the above-defined prodrug, the cytostatic is doxorubicin, paclitaxel, gemcitabin or a camptothecin derivative, the transcription factor inhibitor is a sesquiterpene lactone derivative and the protein-binding group is a maleimide derivative.

According to a preferred embodiment of the prodrug as defined above, the cytostatic is doxorubicin, paclitaxel, gemcitabin or a camptothecin or any derivative thereof, the transcription factor inhibitor is helenalin, budlein A or miller-9E-enolid, or any derivative thereof, and the protein-binding moiety is a maleimide derivative.

Another aspect of the present invention relates to a pharmaceutical composition, comprising the prodrug as defined above, and optionally a pharmaceutically acceptable carrier and/or a pharmaceutically acceptable adjuvent and/or a diluent.

The pharmaceutical composition may for example contain solvents and diluents such as sodium chloride solution or a solution containing any pharmaceutically acceptable buffer. Moreover, the pharmaceutical composition of the present invention may be in any form suitable for administration to a patient, for example in an injectable form, as a tablet or a capsule, or as a composition for inhalation.

According to a specific embodiment, the above-defined pharmaceutical composition is for treatment of a disease selected from the group consisting of cancer, autoimmune diseases, acute or chronic inflammatory diseases or diseases caused by viruses and/or microorganisms.

According to a further specific embodiment, the above-defined pharmaceutical composition is for treatment of cancer.

Another aspect of the present invention relates to the use of the prodrug as defined above in the manufacturing of a pharmaceutical composition for treating or diagnosing a patient suffering from a disease selected from the group consisting of cancer, autoimmune diseases, acute or chronic inflammatory diseases or diseases caused by viruses and/or microorganisms.

According to another embodiment of the present invention, the prodrug as defined above may be comprised in a kit, which may further contain one or more adjuvants, such as a buffer or a pharmaceutically acceptable carrier.

The figure shows:

The prodrug according to the present invention is advantageously capable of binding in situ to a thiol-containing macromolecular carrier such as endogenous albumin, thus enabling a more specific transport to the target tissue in a patient.

Moreover, the presence of at least two different pharmaceutically active compounds allows to improve treatment of a disease in a patient. In particular, by combining two different pharmacologically active compounds in a prodrug being able to bind in situ to a thiol-containing macromolecule such as albumin, it is surprisingly achieved to efficiently accumulate both drugs in the target tissue of the patient and, after cleavage of the active agents, to advantageously reduce at least one of the biochemical mechanisms known to reduce the efficacy of one or more of the active agents employed.

The present invention is illustrated in the following example without any limitation thereto.

EXAMPLES

Example 1

According to the present invention, a dual acting prodrug is prepared comprising the P-glycoprotein inhibitor OC144093 and camptothecin.

In this example, camptothecin and OC144093 are bound to a bifunctional malemide derivative through a peptide spacer that is cleaved by cathepsin B or other proteases. After transport to the tumor cell the prodrugs exert their action through a dual acting principle: OC144093 inhibits the efflux pump P-glycoprotein that is responsible for multidrug resistance thus preventing the efflux of campthothecin and allowing this drug to exert its antitumor efficacy in the tumor cell.

Example 2

According to the present invention, a dual acting prodrug is comprises an amino derivative of the proteasom inhibitor MG-132 (aminobenzoylamide-Leu-Leu-Leu-CHO) and the anticancer agent paclitaxel:

In this example, paclitaxel and the proteasom inhibitor aminobenzoylamide-Leu-Leu-Leu-CHO are bound to a bifunctional malemide derivative through a peptide spacer that is cleaved by cathepsin B or other proteases.

Example 3

Figure 1:
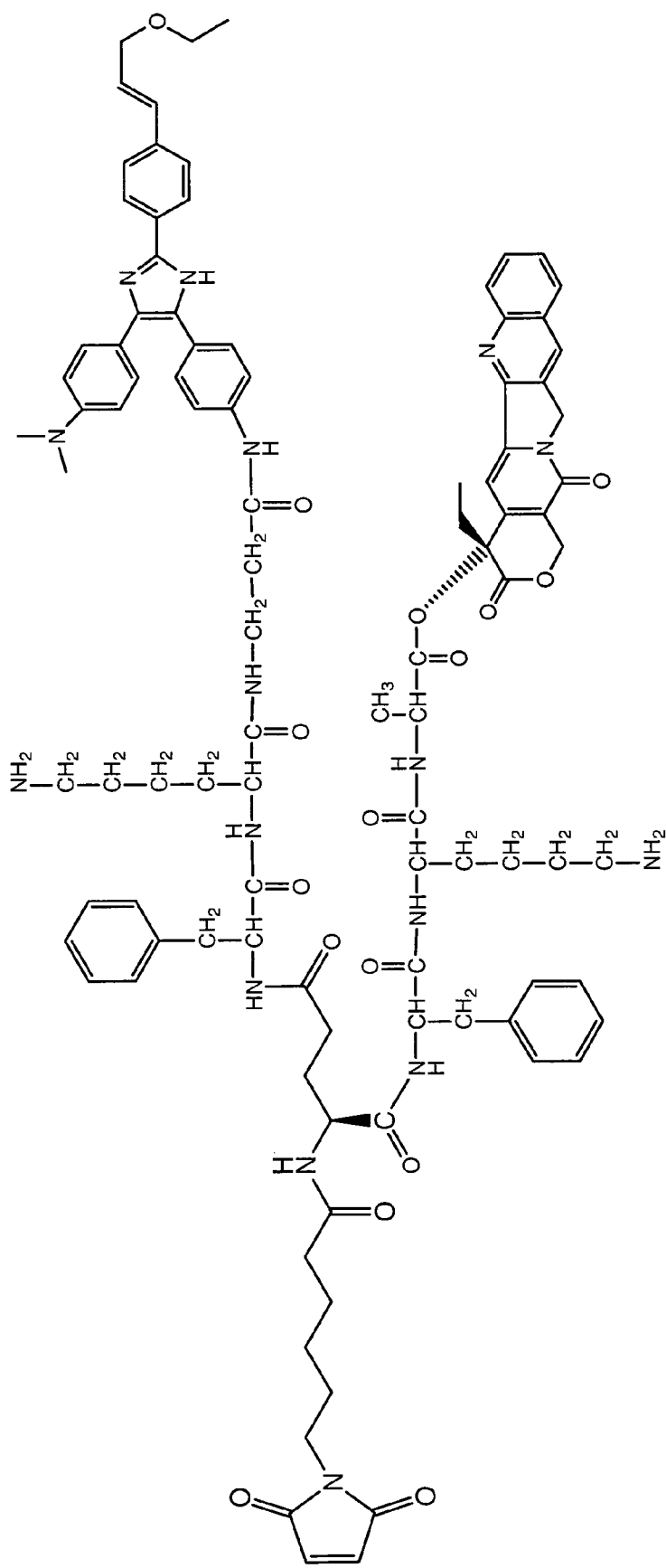
FIG. 1 shows the structure of a dual acting prodrug comprising the P-glycoprotein inhibitor OC144093 and camptothecin.
Figure 2:
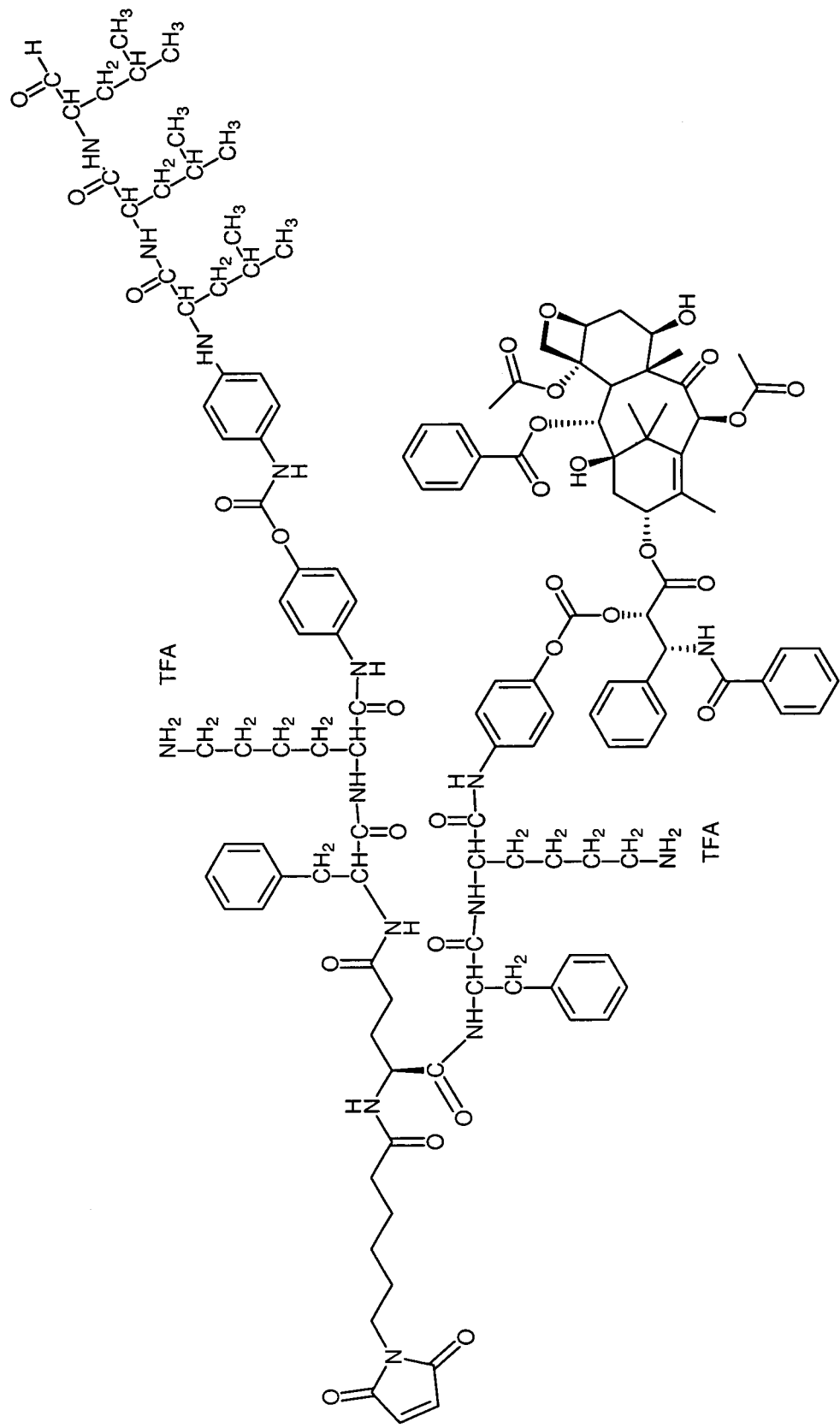
FIG. 2 shows the structure of a dual acting prodrug comprising an amino derivative of the proteasom inhibitor MG-132 (aminobenzoylamide-Leu-Leu-Leu-CHO) and the anticancer agent paclitaxel.
Figure 3:
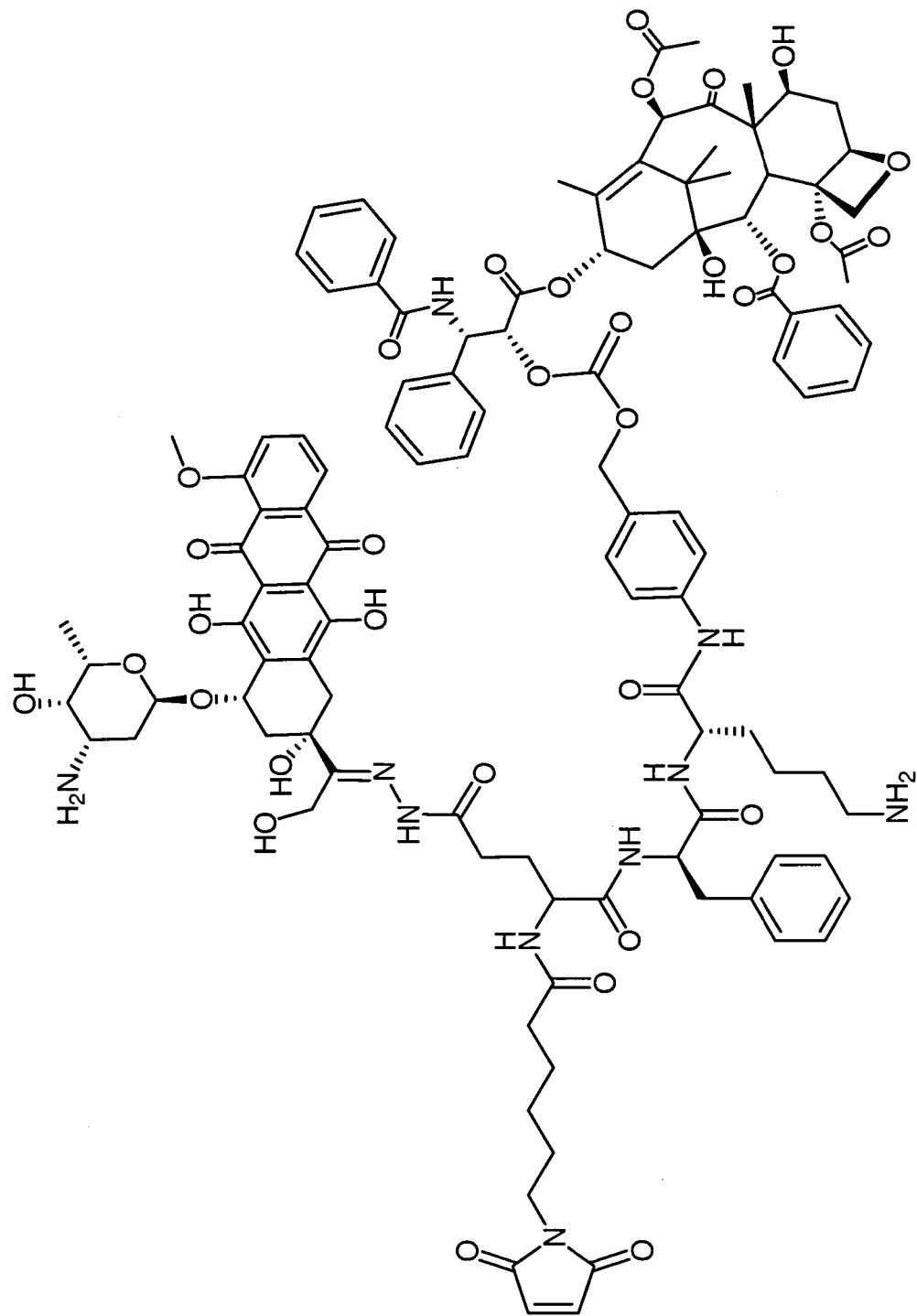
FIG. 3 shows the structure of a dual acting prodrug comprising the two anticancer agents paclitaxel and doxorubicin (12)

According to the present invention, a dual acting prodrug 12 is prepared comprising the two anticancer agents paclitaxel and doxorubicin (see FIG. 3). The pharmaceutically active compounds, i.e. doxorubicin and paclitaxel, are released from the prodrug by cleavage of an acid-labile hydrazone linker and a cathepsin B cleavable dipeptide linker. The prodrug according to the present invention is advantageously capable of binding in situ to a thiol-containing macromolecular carrier such as albumin, thus enabling a more specific transport to the tumor tissue and releasing both doxorubicin and paclitaxel in tumor tissue and tumor cells. In a 72 cytotoxicity assay against HT29 colon carcinoma cells prodrug 12 showed an $IC_{50}$ value in the low nanomolar region ($IC_{50}$~11 nM).

Figure 4A:
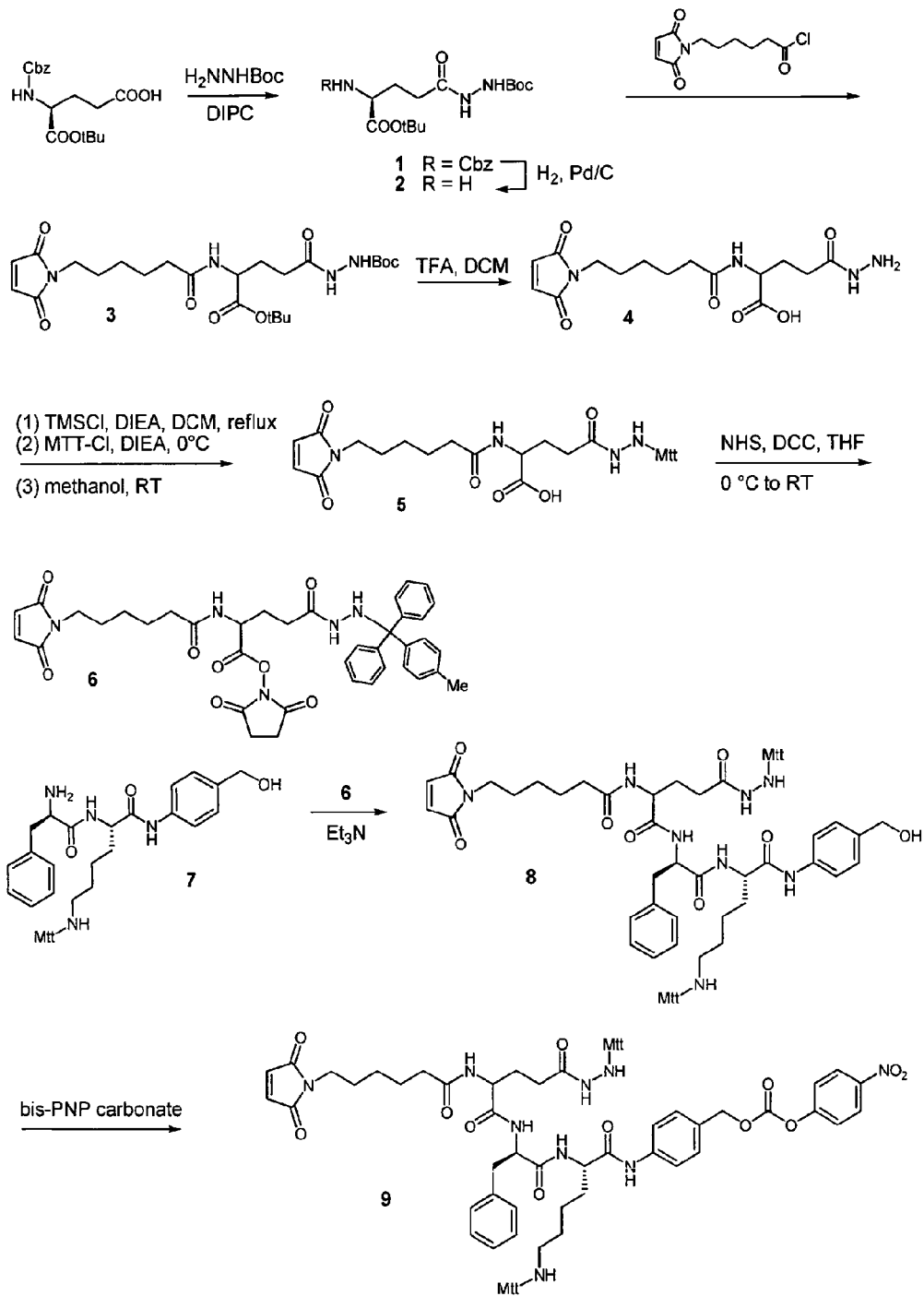
FIGS. 4a and 4b show the synthetic route for obtaining a dual acting prodrug comprising the two anticancer agents paclitaxel and doxorubicin (12)
Figure 4B:
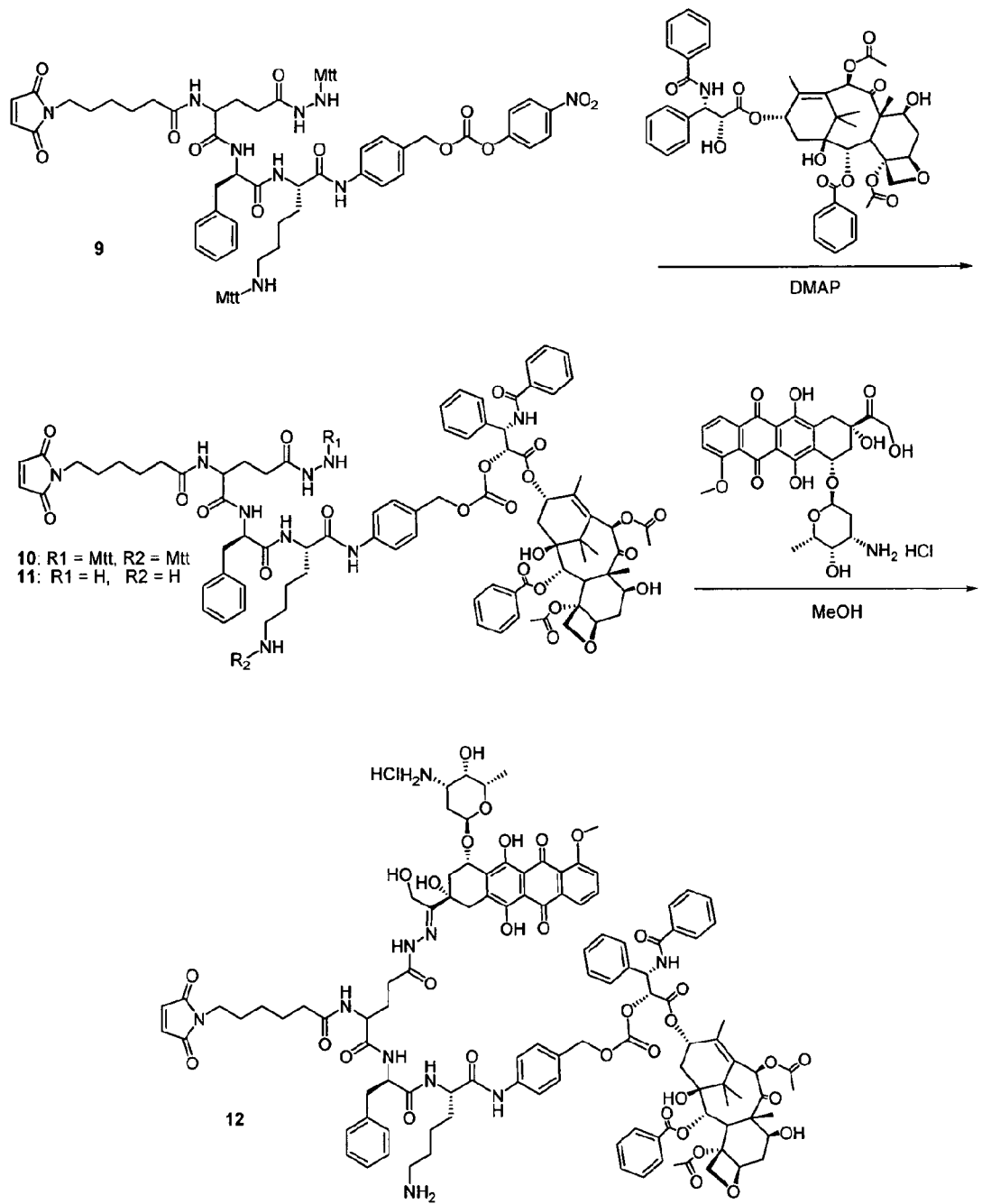

The prodrug 12 was synthesized according to FIGS. 4a and 4b as described below.

Synthesis of EMC-Glu(NHNH-Mtt)-OH (5):

DMAP (0.1 equiv, 14.8 mmol, 1.81 g) and DIPC (1.5 equiv, 222.3 mmol, 34.5 mL) were added under nitrogen atmosphere slowly at 0° C. to a solution of Cbz-Glu-OtBu (148.2 mmol, 50 g) and tert.-butyl carbazate (1.5 equiv, 222.3 mmol, 29.4 g) in dry DCM (100 mL). The mixture was stirred at RT for 16 h. The solid was removed by suction filtration and washed with DCM. The organic layer was extracted with 0.1 M HCl (10×100 mL). The organic phase was then extracted with brine, water, dried and the solvent was removed under reduced pressure to give 1 as a white solid (66.6 g). $C_{22}H_{33}N_3O_7$, Exact Mass: 451.23, MS (ESI): m/e 474.0 $(M+Na)^+$. 1 (60 g) was dissolved under nitrogen in dry methanol (200 mL). Pd/C (10%, 2.5 g) was added and a hydrogen balloon was applied to the flask. The reaction mixture was stirred at RT for 4 d during which the balloons were exchanged with new ones. The solution was then diluted with methanol, filtered over celite and the solvent was removed under reduced pressure. The oily rest was purified by flash chromatography on silica with $CHCl_3$/MeOH 20:1 to give 2 as a white solid (42 g, 50%). $C_{14}H_{27}N_3O_5$, Exact Mass: 317.2, MS (ESI): m/e 318.0 $(M+H)^+$, m/e 340.0 $(M+Na)^+$. The 6-maleimidocaproic acid chloride was prepared from maleimidocaproic acid (82.78 mmol, 17.35 g) and oxalic acid chloride (1.0 equiv, 82.78 mmol, 9.93 mL) in dry DCM (180 mL). Dry triethylamine (82.78 mmol, 11.47 mL) was added at RT under nitrogen atmosphere to a solution of 2 (82.78 mmol, 26.36 g) in dry DCM (300 mL) followed by slow addition of the solution of 6-maleimidocaproic acid chloride. The reaction solution was stirred at RT for 18 h. The solvent was removed under reduced pressure. The oily residue was purified by flash chromatography on silica eluting with EE/hexane (i) 1:1, (i) 2:1, (i) 4:1 to give 3 as a white solid (36 g, 76%). $C_{24}H_{38}N_4O_8$, Exact Mass: 510.27, (ESI): m/e 533.1 $(M+H)^+$. A solution of 3 (32.4 g) and TFA (165 mL) in $CH_2Cl_2$ (165 mL) was stirred at RT for 80 min. The product was precipitated with diethyl ether (4 L) as a TFA-salt. 4 was then collected by suction filtration, washed with ether and dried (20 g, 68%). $C_{15}H_{22}N_4O_6$, Exact Mass: 354.15, (ESI): m/e 355.1 $(M+H)^+$. A stirred suspension of 4 (11 mmol, 5 g,) in dry DCM (50 mL) under nitrogen atmosphere at RT was treated with trimethylsilyl chloride (2.1 equiv, 23.1 mmol, 3 mL) and DIEA (1.05 equiv, 11.55 mmol, 1.9 mL). The mixture was heated at reflux for 1 h, and then cooled to 0° C. DIEA (3.1 equiv, 63.8 mmol, 5.8 mL) was added, followed by 4-metyltrityl chloride (1.05 equiv, 11.55 mmol, 3.41 g). The reaction was stirred at RT for 16 h. Methanol (50 mL) was added and the solution was stirred for 5 min. The solvent was evaporated at 30° C., and the residue was partitioned between DCM and pH 5 buffer (acetate). The organic phase was washed with pH 5 buffer, water, and brine, dried and the solvent was evaporated. The oily residue was purified by flash chromatography on silica eluting with $CHCl_3$/$CH_3OH$ (10:1) to give 5 as pale yellow foam (4.5 g, 83%). $C_{35}H_{38}N_4O_6$, Exact Mass: 610.28, (ESI): m/e 633.1 $(M+Na)^+$. $^{13}C$ NMR (100.61 MHz, CDCl$_3$): δ=21 (−, CH$_3$), 25, 26, 28, 37, 39, 41, 44 (−, 7×CH$_2$), 55 (+, CONHC$\overline{\text{H}}$), 72 (+, Ar$_3$C), 135 (+, CH CH), 127, 128, 129, 130 (−, Ar), 138, 141, 144 (−, Ar), 170, 171, 174 (−, HOCO, 4×NCO). A stirred solution of 5 (6.22 mmol, 3.8 g) and HOSu (1.05 equiv, 6.60 mmol, 755 mg) in dry THF (25 mL) at 0° C. was treated with DCC (1.05 equiv, 6.60 mmol, 1.36 g). After 20 min, the mixture was allowed to warm to RT and was stirred for 16 h. The solid by-product was filtered off, washed with dry THF, and the solvent was evaporated. The residue was purified by flash chromatography on diol, eluting with THF/hexane (1:1) to furnish 6 as a white solid (2.70 g, 62%). C$_{39}$H$_{41}$N$_5$O$_8$, Exact Mass: 707.30, (ESI): m/e 730.2 (M+Na)$^+$.

Synthesis of EMC-Glu(NH-NHMtt)-Phe-Lys(MMT)-PABC-PNP (9):

A stirred solution of 7 (1.11 mmol, 0.73 g) and 6 (1.2 equiv, 1.33 mmol, 0.95 g) in dry THF (20 mL) was treated at RT with dry Et$_3$N (1.0 equiv, 1.11 mmol, 155 μL). The mixture was allowed to stir at RT for 20 h and then the solvent was evaporated, and the residue was purified by flash chromatography on silica gel eluting with CHCl$_3$/CH$_3$OH (15:1)+2% Et$_3$N to give 8 as a white solid (0.93 g, 75%). C$_{77}$H$_{82}$N$_8$O$_8$, Exact Mass: 1246.63, (ESI): m/e 1247.4 (M+H)$^+$. 8 (0.2 mmol, 255 mg) and bis-PNP carbonate (5 equiv, 1 mmol, 348 mg) were dissolved under nitrogen atmosphere at RT in dry DCM (15 mL) and treated with DIEA (3 equiv, 0.6 mmol, 102 μL). The reaction mixture was stirred for 3 d. The solvent was removed and the residue was purified by flash chromatography on diol eluting with THF/hexane (3:2) to give 9 as a pale yellow solid (150 mg, 52%). C$_{84}$H$_{85}$N$_9$O$_{12}$, Exact Mass: 1411.63, (ESI): m/e 1412.2 (M+H)$^+$.

Synthesis of 12:

DMAP (417 mg) was added to a solution of 9 (550 mg) and paclitaxel (332 mg) in dry DCM (20 mL). The solution was stirred at RT for 20 h. The product was precipitated from ether and then purified by flash chromatography on silica eluting with CHCl$_3$/MeOH 20:1 to give 10 as a solid (200 mg, 67%). A solution of 10 (180 mg) in 1% TFA in DCM (2 mL) was stirred at RT for 1 h. The product 11 was precipitated from ether as a white solid (100 mg, 66%). C$_{85}$H$_{99}$N$_9$O$_{23}$, Exact Mass: 1613.69, (ESI): m/e 1636.3 (M+Na)$^+$11 (5 equiv, 20 mg) and doxorubicin HCl (1 equiv, 1.2 mg) were dissolved in dry methanol (1 mL) and the reaction solution was stirred at RT for 18 h. The product was precipitated from isopropanol/ether and then purified by HPLC (25 cm Synergi 4 u Max-RP 80A (Phenomenex), flow rate: 1 mL/min, mobile phase A: pH 7/AcN 80:20, mobile phase B: pH7/AcN 40:60, retention time: 29.63 min) to yield 3 mg 12. C$_{114}$H$_{127}$ClF$_3$N$_{10}$O$_{35}$, Exact Mass: 2138.85, (ESI): m/e 2140.0 (M+H)$^+$.

---

The invention claimed is:

1. A prodrug comprising
   (i) at least a first pharmaceutically and/or diagnostically active compound, the first pharmaceutically and/or diagnostically active compound is a cytostatic agent selected from the group consisting of N-nitrosoureas, the anthracyclines doxorubicin, daunorubicin, epirubicin, idarubicin, mitoxantrone and ametantrone; the alkylating agents chlorambucil, bendamustine, melphalan, and oxazaphosphorines; the antimetabolites 5-fluorouracil, 2'-deoxy-5-fluorouridine, cytarabine, cladribine, fludarabine, pentostatine, gemcitabine and thioguanine; the folic acid antagonists methotrexate, raltitrexed, pemetrexed and plevitrexed, the taxanes paclitaxel and docetaxel; the camptothecins topotecan, irinotecan, 9-aminocamptothecin and camptothecin; the Vinca alkaloids vinblastine, vincristine, vindesine and vinorelbine; calicheamicins; maytansinoids; auristatins; epothilones; bleomycin, dactinomycin, plicamycin, mitomycin C and cis-configured platinum(II) complexes;
   (ii) at least a second pharmaceutically and/or diagnostically active compound, the second pharmaceutically and/or diagnostically active compound is independently selected from the group consisting of a cytostatic agent, a cytokine, an immunosuppressant, an antirheumatic, an antiphlogistic, an antibiotic, an analgesic, a virostatic, or an antimycotic agent, a transcription factor inhibitor, a cell cycle modulator, a MDR modulator, a proteasome or protease inhibitor, an apoptosis modulator, an enzyme inhibitor, an angiogenesis inhibitor, a hormone, a radioactive substance, a light emitting substance, and a light absorbing substance;
   (iii) two or more cleavable linkers independently selected from the group of enzymatically cleavable peptide sequences and cleavable linkers containing at least one acid-sensitive bond, wherein (a) the enzymatically cleavable peptide sequence selected from the group consisting of Arg, Arg-Arg, Phe-Arg, Phe-Cit, Ile-Pro Lys, Lys-Lys, Arg-Lys, Ala-Leu-Ala-Leu [SEQ ID NO:1], Phe-Lys, Phe-Lys-Ala, Val-Cit, Val-Arg, Ala-Phe-Lys, D-Ala-Phe-Lys, Met, Met-Met, Phe-Met, Tyr-Met, Ala-Met, Ala-Phe-Met, Phe-Ala-Met, Ala-Tyr-Met, Phe-Tyr-Met, Ser-Ser-Tyr-Tyr-Ser-Arg [SEQ ID NO:2], Phe-Pro-Lys-Phe-Phe-Ser-Arg-Gln [SEQ ID NO:3], Lys-Pro-Ile-Glu-Phe-Nph-Arg-Leu [SEQ ID NO:4], Gly-Pro-Leu-Gly-Ile-Ala-Gly-Gln [SEQ ID NO:5], Gly-Pro-Leu-Gly-Ile-Ala-Gly-Gln [SEQ ID NO:6], and Gly-Phe-Leu-Gly [SEQ ID NO:7] and (b) the cleavable linker containing at least one acid-sensitive bond selected from ester, acetal, ketal, imine, hydrazone, acylhydrazone and sulfonylhydrazone bonds and bonds containing a trityl group;

(iv) a protein-binding group that covalently binds to a serum protein, an antibody or antibody fragments, a synthetic polymer, a peptide, a growth factor, a polysaccharide, or a sugar, the protein-binding group is selected from the group consisting of a maleinimide group, a halogenacetamide group, a halogenacetate group, a pyrildylthio group, a vinylcarbonyl group, an aziridin group, a disulfide group, a substituted or unsubstituted acetylene group, and an N-hydroxysuccininide ester group, wherein the first and the second pharmaceutically and/or diagnostically active compounds are each bound to a cleavable linker, and wherein the first and the second pharmaceutically and/or diagnostically active compounds are different from each other.

2. The prodrug according to claim 1, wherein the second pharmaceutically and/or diagnostically active compound is a cytostatic agent selected from the group consisting of N-nitrosoureas, the anthracyclines doxorubicin, daunorubicin, epirubicin, idarubicin, mitoxantrone and ametantrone; the alkylating agents chlorambucil, bendamustine, melphalan, and oxazaphosphorines; the antimetabolites 5-fluorouracil, 2'-deoxy-5-fluorouridine, cytarabine, cladribine, fludarabine, pentostatine, gemcitabine and thioguanine; the folic acid antagonists methotrexate, raltitrexed, pemetrexed and plevitrexed, the taxanes paclitaxel and docetaxel; the camptothecins topotecan, irinotecan, 9-aminocamptothecin and camptothecin; the Vinca alkaloids vinblastine, vincristine, vindesine and vinorelbine; calicheamicins; maytansinoids; auristatins; epothilones; bleomycin, dactinomycin, plicamycin, mitomycin C and cis-configured platinum(II) complexes.

3. The prodrug according to claim 1, wherein the protein-binding group binds in situ to cysteine-34 of albumin.

4. The prodrug according to claim 1, wherein at least one of the first or second pharmaceutically and/or diagnostically active compounds contains one or more radionuclides, one or more positron emitters, one or more NMR contrast agents, one or more fluorescent compound(s), or one or more near-infrared contrast agents.

5. A pharmaceutical composition comprising the prodrug according to claim 1, and optionally a pharmaceutically acceptable carrier and/or a pharmaceutically acceptable adjuvent and/or a diluent.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic-Preferred peptide equence
      incorporated in the prodrug

<400> SEQUENCE: 1

Ala Leu Ala Leu
1

<210> SEQ ID NO 2
<211> LENGTH: 6
<212> TYPE: PRT
<213> ORGANISM: Artificial Sequence
<220> FEATURE:
<223> OTHER INFORMATION: Synthetic-Preferred peptide equence
      incorporated in the prodrug

<400> SEQUENCE: 2

Ser Ser Tyr Tyr Ser Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic-cleavable linker

<400> SEQUENCE: 3

Phe Pro Lys Phe Phe Ser Arg Gln
1               5

<210> SEQ ID NO 4
<211> LENGTH: 8
```

```
<212> TYPE: PRT
<213> ORGANISM: Artificial Sequence
<220> FEATURE:
<223> OTHER INFORMATION: Synthetic-Preferred peptide sequence
      incorporated in the prodrug
<220> FEATURE:
<221> NAME/KEY: nph
<222> LOCATION: (6)..(6)
<223> OTHER INFORMATION: x = nitrophenylalanine

<400> SEQUENCE: 4

Lys Pro Ile Glu Phe Xaa Arg Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic-Preferred peptide sequence
      incorporated in the prodrug

<400> SEQUENCE: 5

Gly Pro Leu Gly Ile Ala Gly Gln
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic-Preferred peptide sequence
      incorporated in the prodrug

<400> SEQUENCE: 6

Gly Pro Gln Gly Ile Trp Gly Gln
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic-Preferred peptide sequence
      incorporated in the prodrug

<400> SEQUENCE: 7

Gly Phe Leu Gly
1
```